United States Patent
Goldberg

(10) Patent No.: US 11,540,710 B2
(45) Date of Patent: Jan. 3, 2023

(54) SYSTEM AND METHOD FOR TESTING PERIPHERAL VISION

(71) Applicant: Jeffrey Goldberg, Menlo Park, CA (US)

(72) Inventor: Jeffrey Goldberg, Menlo Park, CA (US)

(*) Notice: Subject to any disclaimer, the term of this patent is extended or adjusted under 35 U.S.C. 154(b) by 578 days.

(21) Appl. No.: 16/087,327

(22) PCT Filed: Mar. 21, 2017

(86) PCT No.: PCT/US2017/023349
§ 371 (c)(1),
(2) Date: Sep. 21, 2018

(87) PCT Pub. No.: WO2017/165373
PCT Pub. Date: Sep. 28, 2017

(65) Prior Publication Data
US 2020/0329959 A1      Oct. 22, 2020

Related U.S. Application Data

(60) Provisional application No. 62/311,140, filed on Mar. 21, 2016.

(51) Int. Cl.
*A61B 3/00* (2006.01)
*A61B 3/024* (2006.01)
*A61B 3/113* (2006.01)
*A61B 3/16* (2006.01)

(52) U.S. Cl.
CPC .......... *A61B 3/0033* (2013.01); *A61B 3/0025* (2013.01); *A61B 3/0091* (2013.01); *A61B 3/024* (2013.01); *A61B 3/113* (2013.01); *A61B 3/165* (2013.01)

(58) Field of Classification Search
CPC ....... A61B 3/0033; A61B 3/0025; A61B 3/02; A61B 3/0091; A61B 3/024; A61B 3/113; A61B 3/165; A61B 3/032
USPC .......................... 351/222, 246, 224, 237, 201
See application file for complete search history.

(56) References Cited

U.S. PATENT DOCUMENTS

| | | | |
|---|---|---|---|
| 7,367,673 B2 * | 5/2008 | McGrath | A61B 3/0091 351/205 |
| 2009/0180071 A1 * | 7/2009 | Fateh | A61B 3/024 351/203 |
| 2012/0081662 A1 * | 4/2012 | Reichow | A61B 3/0033 351/203 |
| 2012/0133890 A1 * | 5/2012 | Rathjen | A61B 3/113 351/209 |

(Continued)

OTHER PUBLICATIONS

International Search Report and Written Opinion dated Jun. 21, 2017, issued in connection with corresponding International Application No. PCT/US2017/023349 (9 pages total).

*Primary Examiner* — Travis S Fissel
(74) *Attorney, Agent, or Firm* — Stuart H. Mayer; Mayer & Williams PC

(57) ABSTRACT

Systems and methods according to present principles use touchscreen-based devices such as tablet computers or other computers incorporating touchscreens to both run the test and to receive input/output. It will be understood that any such device may be employed, so long as a display, means for user input, and means for eye tracking, are provided, and so long as its display screen is large enough to effectively test visual field.

17 Claims, 4 Drawing Sheets

(56) References Cited

U.S. PATENT DOCUMENTS

2013/0155376 A1   6/2013  Huang et al.
2014/0320817 A1  10/2014  Kiderman et al.
2016/0045108 A1*  2/2016  Wu ........................ A61B 3/112
                                                            351/210

* cited by examiner

SYSTEM AND METHOD FOR TESTING PERIPHERAL VISION

CROSS-REFERENCE TO RELATED APPLICATIONS

This application claims benefit of priority of U.S. Provisional Patent Application Ser. No. 62/311,140, entitled "SYSTEM AND METHOD FOR TESTING PERIPHERAL VISION", filed Mar. 21, 2016, owned by the owner of the present application and herein incorporated by reference in its entirety.

BACKGROUND

Peripheral vision, as opposed to central vision, relates to the ability to see objects and movement on the side extremes of one's vision, i.e., not in the direct line of sight.

The peripheral retina of the eyes is generally responsible for peripheral vision. The loss of peripheral vision is termed "tunnel vision", and can be associated with glaucoma or other deteriorations of the retina or optic nerve. Thus, one potential test for glaucoma involves testing peripheral vision, and such has been implemented by perimetry tests, i.e., visual field testing.

However, such are generally associated with a complicated piece of capital equipment called a "Perimeter", which is generally bulky and not suited for portable use. Portable and inexpensive equipment are generally highly desired as trends towards value and outcome based medicine continue.

SUMMARY OF THE INVENTION

In an implementation, systems and methods according to present principles use touchscreen-based devices such as tablet computers or other computers incorporating touchscreens to both run the test and to receive input/output. It will be understood that any such device may be employed, so long as a display, means for user input, and means for eye tracking, are provided, and so long as its display screen is large enough to effectively test visual field.

In one aspect, the invention is directed towards a method of testing the visual field of a user, including: displaying a still element on a touch screen user interface; detecting if a user's eye or eyes are fixated on the still element; if the user's eye or eyes are not fixated on the still element, displaying an instruction to the user to look at the still element; if the user's eye or eyes are fixated on the still element, and during the time that the user's eye or eyes are fixated on the still element, displaying a flash element at a location in a peripheral vision at a first given time; receiving a signal indicating that a user saw the flash element while the user's eye or eyes were fixated on the still element; repeating the displaying a flash element at the same or another location in the peripheral vision and the receiving a signal for one or more subsequent given times; determining an indication of the visual field of the user based on the received signals.

Implementations of the invention may include one or more of the following. The receiving a signal may include receiving a tap or click indication from the user interface, or receiving an auditory indication from the user interface. The method may further include determining whether the receiving a signal occurred within a first duration following the first given time, and the determining an indication may be further based on the determining whether the receiving a signal occurred within a first duration following the first given time. The determining an indication may include calculating a visual field. The method may further include displaying an indication of the calculated visual field on the user interface. The method may further include determining a measure associated with glaucoma based on the calculated visual field. The method may further include determining a measure associated with eye or vision or other defects or maladies based on the calculated visual field. The eye or vision defect or malady may involve the peripheral vision. The method may further include determining if an eye movement has occurred during the fixation, and if so, determining a type of eye movement detected as part or all of the movement. The method may further include basing a portion of the determining an indication on the presence and type of determined eye movements.

In another aspect, the invention is directed towards a computer readable medium, including instructions for causing a computing environment to perform the method described above. The instructions may be downloadable from an online resource.

In another aspect, the invention is directed towards a method of testing the visual field of the user, including: detecting a user input indicating that a visual field test should begin; displaying a first element on a touch screen user interface; detecting if a user's eye or eyes are looking at the first element, and determining a first time duration between the display of the first element and the detecting; repeating the displaying and detecting if a user's eyes are looking at the respective element steps for a plurality of subsequent sequential elements; based on locations of the sequential elements, and/or distances therebetween, and the determined time durations, and the determined angles of user saccades, and the determined distances of user saccades, determining an indication of a visual field of the user.

Implementations of the invention may include one or more of the following. The method may further include if the user's eye or eyes are detected to be not looking at the displayed element, displaying an instruction to the user to look at the displayed element. The detecting if the user's eye or eyes are looking at the element may include detecting if the user's eye or eyes are fixated on the element. The detecting if the user's eye or eyes are looking at the element may include detecting if the user's eye or eyes moved in a direction towards the element. The detecting if the user's eye or eyes moved in a direction towards the element may include detecting if the user's eye or eyes moved in a direction from a previous element to the subsequent element. The method may further include determining a type of eye movement detected as part or all of the movement. The method may further include excluding certain types of eye movements from the detecting if a user's eye or eyes are looking at the element step.

In a related aspect, the invention is directed towards a computer readable medium, including instructions for causing a computing environment to perform the above method. Such instructions may be downloadable from an online resource.

Advantages of certain implementations of the invention may include one or more of the following. Systems and methods according to present principles provide significantly inexpensive and convenient ways to perform visual field testing, e.g., tests of peripheral vision, for the diagnosis of eye and vision ailments including glaucoma.

BRIEF DESCRIPTION OF THE DRAWINGS

Like reference numerals refer to like elements throughout. Elements are not to scale unless specifically noted.

DETAILED DESCRIPTION

As noted above, systems and methods according to present principles may employ in an implementation touchscreen-based devices such as tablet computers or other computers incorporating touchscreens to both run the test and to receive input/output. It will be understood that any such device may be employed, so long as a display, means for user input, and means for eye tracking, are provided, and so long as its display screen is large enough to effectively test visual field.

Two embodiments are illustrated in the attached figures. However, given this teaching, other embodiments will also be understood.

Figure 1:
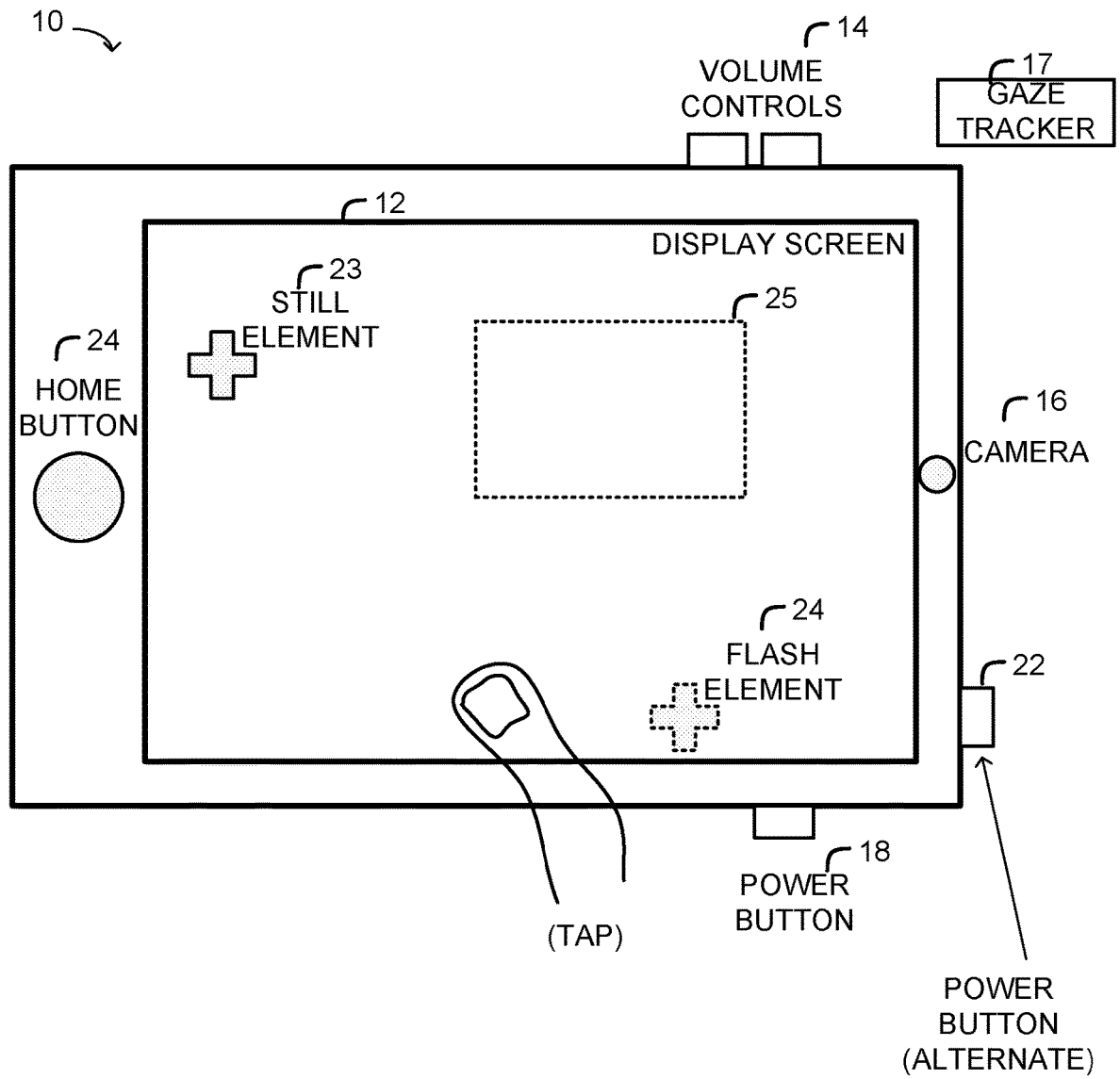
FIG. 1 illustrates a touch screen computer implementing one embodiment of systems and methods according to present principles.

Referring first to FIG. 1, a tablet computer 10 having a display screen 12 is illustrated. The tablet computer may be, e.g., an iPad®, an Android or Windows tablet, or the like. As may be seen in the figure, volume controls 14 may be provided, as well as power button 18 or 22 or both. A camera 16 may be provided, in the same may be employed to receive a visual image of the user as well as in some implementations to implement gaze tracking by visually tracking the position of the user's eye(s), such as by use of a gaze tracker 17. A home button 24 may be provided to redirect the screen to a home page.

The display screen 12 may implement a user interface on which users may both view rendered items as well as interact with a testing application 25, e.g., by touching the touch screen UI. The testing application 25 as indicated schematically, and it will be understood that the same can cause the rendering of a still element 23, a flash element 24, as well as other elements according to implementation, as well as to receive user input, e.g., as may be detected and/or measured on the touchscreen 12.

For example, a patient may be guided with appropriate instructions on the user interface (touchscreen 12) to look at various elements on the screen and also to interact with displayed elements. For example, as shown in the figure, a still element 23 is displayed on the screen. The still element 23 is displayed in a continuous fashion. A flash element 24 may also be displayed on the screen, but the same is only displayed intermittently, e.g., as a flash. The locations of the still element and the flash element may vary, but generally, the more distant the flash element from the still element, the farther afield (from the field of view) the test is observing.

In one exemplary test, the user may be instructed to view the still element 23 and then tap the screen 12 when the flash element 24 comes into view. Other user indications of the viewer seeing the flash element may also be provided, e.g., including clicking a mouse or saying an audible word or phrase. The ability of the user to see the flash element while staring at the still element is indicative of how much peripheral vision the user possesses.

In an advanced implementation, the eye movements may be tracked, such as by the camera 16 or by other eye tracking devices and methods, and the system may wait for the eyes to fixate on the still element prior to displaying or flashing any of the flash elements. The gaze tracking or eye tracking may detect user eye fixation on the still element and may further detect, measure, or calculate user eye fixation on the flash element.

In this case, the act of fixation is not necessarily the eyes not moving at all, since if the device or head moves, the eyes generally move to compensate. Rather, here "fixation" may refer to the eyes either not moving or making slight smooth pursuits to compensate for head/device movement. The system may then wait for the user to tap the screen to confirm he or she is ready to start. Once the test begins, the patient fixates on the still element. As long as the patient is "fixated" on the still element, the system will present, in his or her peripheral view, flash elements 24 at various distances and angles from the still element 23.

When flash elements appear, the system tests to determine if the patient taps the screen in response, and the test may also include consideration of how much time was taken to see and respond to the flash element. If the patient looks away, e.g., a saccadic movement, from the still element, the system may stop the test and ignore the tapping of the screen. The patient may then be notified of the looking away and requested to look at the still element again to continue the test. These and other instructions to the patient may be provided by texted displayed on the screen or by audio indicators and/or notifications.

The still and flash elements may be of varying color, brightness, contrast against background, duration in time, and/or size, and may be static in any of these parameters, or varying in any of these parameters, with the goal of testing different elements of vision or variably testing or capturing the patient's attention.

Figure 3:
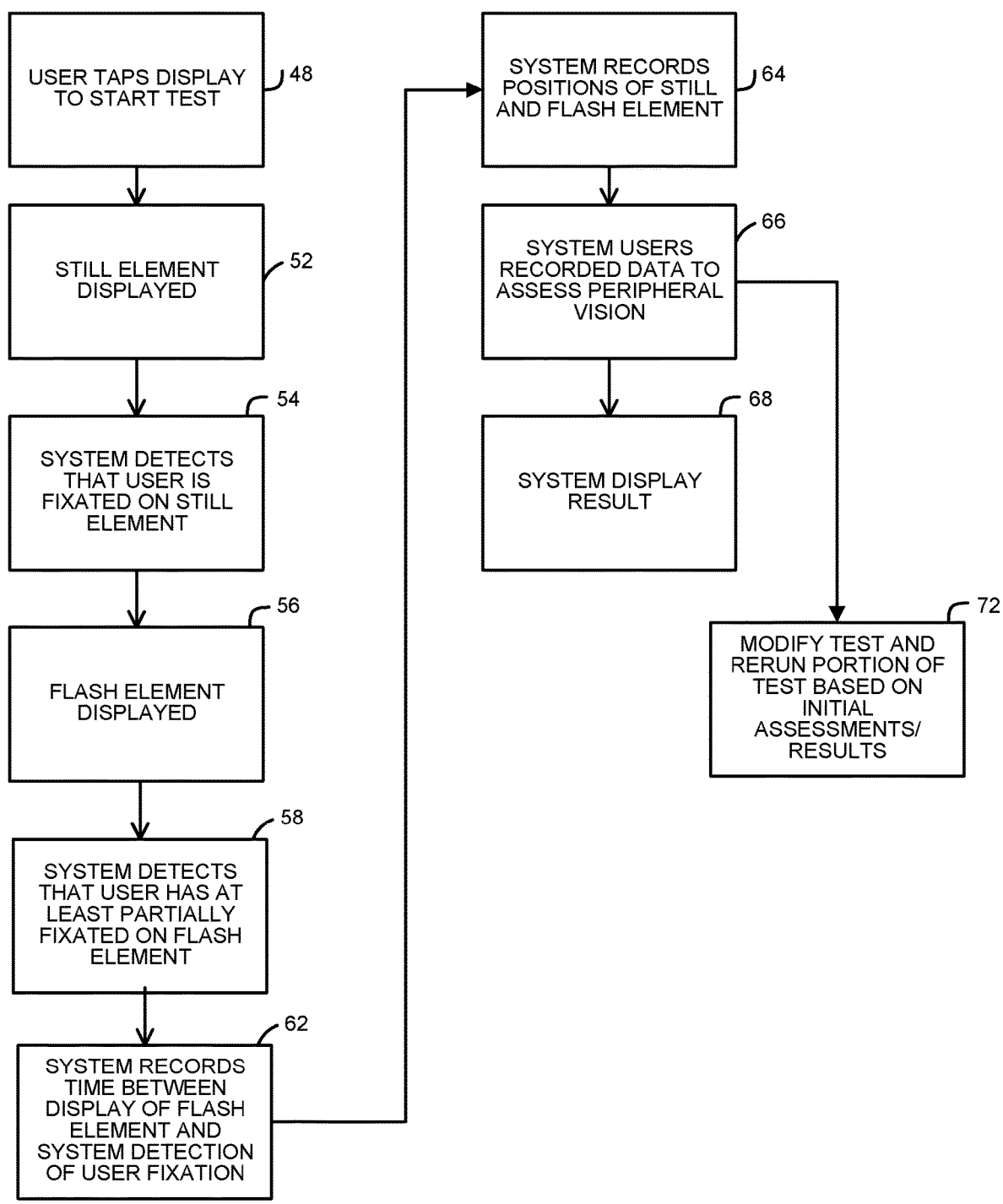
FIG. 3 is a flowchart illustrating a method in which the system of FIG. 1 may be employed.

An exemplary method of the test is provided by the flowchart 20 of FIG. 3. In a first step, the user taps the display to commence the test (step 48). The still element may then be displayed (step 52). The system begins to detect whether the user has fixated on the still element, and once the system has detected such fixation, step 54 is complete and flow passes to step 56. In step 56, a flash element is displayed. The location of the flash element, as well as its duration, may be programmed or selected in a random process by the system and method.

The system may then detect that the user has at least partially fixated on the flash element (step 58). This step may be performed in various ways. For example, in one implementation, the system determines if the user has tapped on the touchscreen, and the tap is accepted as an indication that the user has seen the flash element. In another implementation, a gaze tracker or other detector may be employed to determine if the user has fixated on the flash element. Other techniques will also be understood. The system may then record the time between the display of the flash element and the detection of user fixation on the same (step 62). This step is optional, and the time may not be necessary in every assessment. Generally, however, whether a user has seen a flash element is important to record, as well as some indication of a geometric relationship between the still element and the flash element. In some cases, as peripheral vision may depend on the rotational status of a user's eyes, information about the rotational position of the user's eyes may be recorded as well, and the same used in combination with the position of the still element and the position of the flash element, as well as whether the user detected seeing the flash element, in the general assessment of user peripheral vision.

In some cases, the time notation is simply used to determine if a next element should be displayed, e.g., if a user has not seen the flash element and the test should thus continue after a predetermined period of time. In other cases, the time taken to see and respond may be used in a calculation of other aspects of the visual acuity and/or peripheral vision function of the user, e.g, response time or saccade time and direction from the still element to the flash element, or the like. For example, the faster speed and/or more accurate saccade direction with which a user reacts may be taken as evidence of better detection of the flash element and thus better peripheral vision.

As noted, the system may record positions of the still and flash elements (step 64), and finally the system may use the recorded data to provide an assessment of peripheral vision (step 66). The system may then display a result (step 68). The decline in the speed, or accuracy of the results reflected in the assessment may be taken as a reflection of a decline in the function of the visual acuity and/or peripheral vision function.

To the system and method may provide an iterative process by which a coarse assessment is made of a user's peripheral vision, e.g., using a preprogrammed set of flash elements, followed by a finer assessment. For example, an initial assessment may be the same for everyone, and may cause the user to view a predefined set of flash elements in a predetermined set of locations for a predetermined period of time. Depending on the results of this assessment, the system may branch into performing other tasks as indicated by the results of the first test, including modifying the test and rerunning portions of the test based on initial assessments and results (step 72). For example, the results of the first test may show that the user's peripheral vision is worse on the right side than on the left side. This may be confirmed in the second series of tests by rendering flash elements further out on the right and left-hand sides of the screen and determining a patient's ability to see the same.

Figure 2:
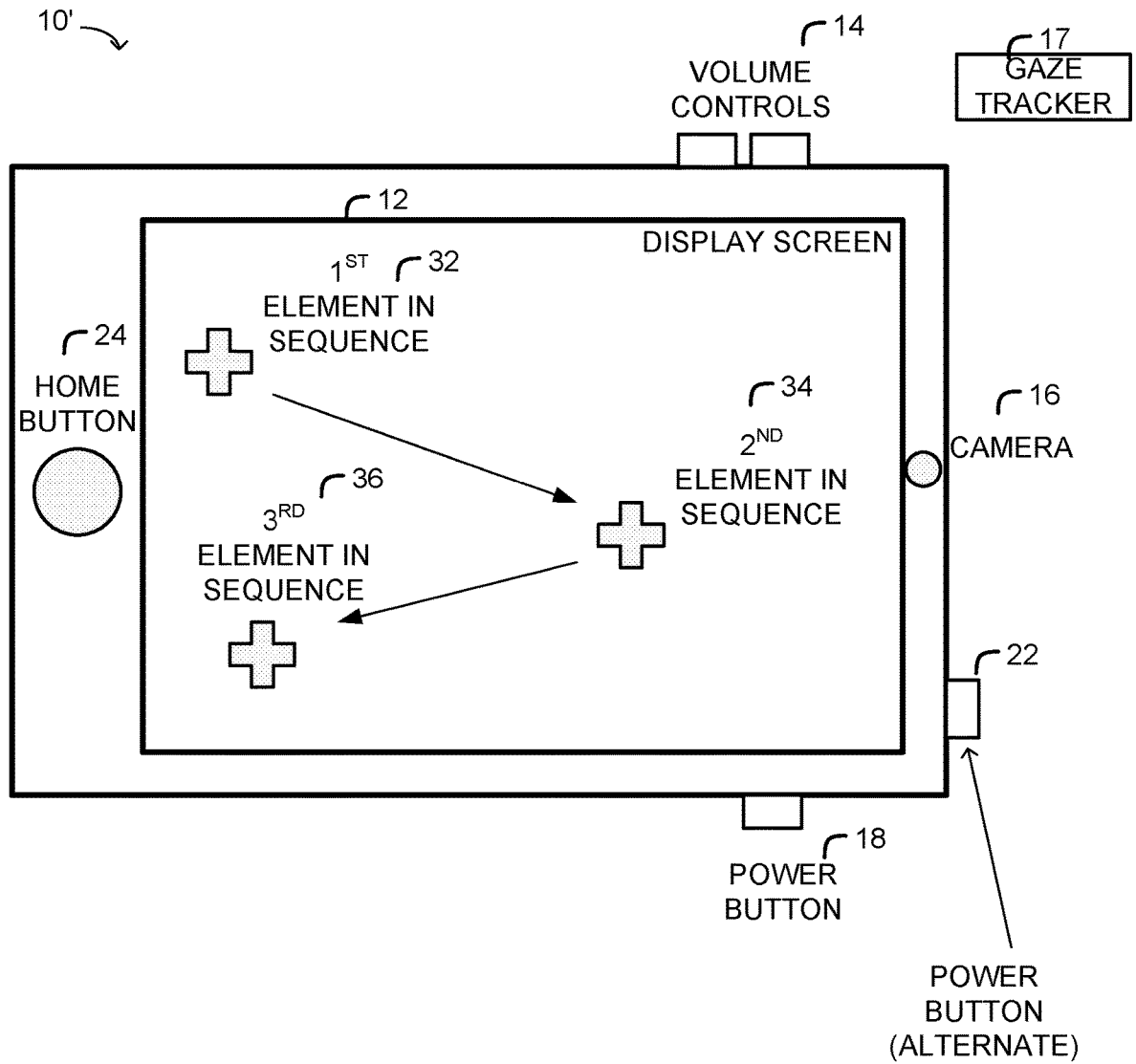
FIG. 2 illustrates a touch screen computer implementing another embodiment of systems and methods according to present principles.

Referring next to the system 10' of FIG. 2, a tablet computer is again employed, but a different type of test is indicated. In this approach, instead of tapping the device when a new or flash element appears, the patient is instructed and expected to change their gaze and to look at such flash elements that appear in the peripheral view. In FIG. 2, a first element in a sequence is shown as element 32, and a second element in the sequence is shown as element 34. A third element is subsequently shown as element 36. It is noted that these flash elements are displayed in a sequence.

Using a gaze tracker or in some cases also (or instead) using user tapping of the touchscreen 12, the system times the look response to the appearance of the new element to evaluate if the patient actually saw the new element and responded to its appearance. For this reason gaze tracking may be particularly useful in this implementation. In particular, the system need not measure if the user looked exactly at the new flash element, but rather if the user responded to its appearance by looking towards it. Important variables measured will include time, as again a timing element may be employed to determine how long it took for the user to respond, as well as features of the eye movement saccade including speed, direction or vector.

The still and flash elements may be of varying color, brightness, contrast against background, duration in time, and/or size, and may be static in any of these parameters, or varying in any of these parameters, with the goal of testing different elements of vision or variably testing or capturing the patient's attention. In an alternative but related implementation, the patient may be guided to always return to the same "origin" fixation point each time, or as noted the test could segue from point to point, changing brightness or size, and over this constantly moving format, calculate the visual field (see FIG. 2).

The calculations that go into the assessment of results and determination of the quality of the peripheral vision, or if determined multiple times over intervals of time, the increase or decrease in the quality of the peripheral vision, will include whether a saccade to the next point occurs, measured as "yes" or "no" where "yes" will have some limits, for example, that it must occur within 1 second and ideally within 500 milliseconds of the appearance of that next point, and that it must demonstrate a saccade in the direction of that next point, measured as degrees of deviation that must be within 30 degrees and ideally within 5 degrees of the direction of that next point, and that it must reach the distance of that next point, generally within plus or minus 25% of the full distance and ideally within 10% of the full distance, in some cases within a predetermined time period. Measures will also include if there are re-fixation movements or additional saccades to complete the fixation onto that next spot. In addition to summing these measures as "yes" or "no" for each spot, the raw data for the measures can be used to assess the quality of vision in each direction from fixation, such that measures of shorter time (e.g. closer to 200 milliseconds), closer saccade direction (e.g. closer to 0 degrees of deviation), and closer distance (e.g. exactly at the full distance), as well as a number of any needed additional re-fixation movements or saccades (e.g. 0 additional saccades needed) will be indicators of better visual function in that area of the peripheral vision.

Figure 4:
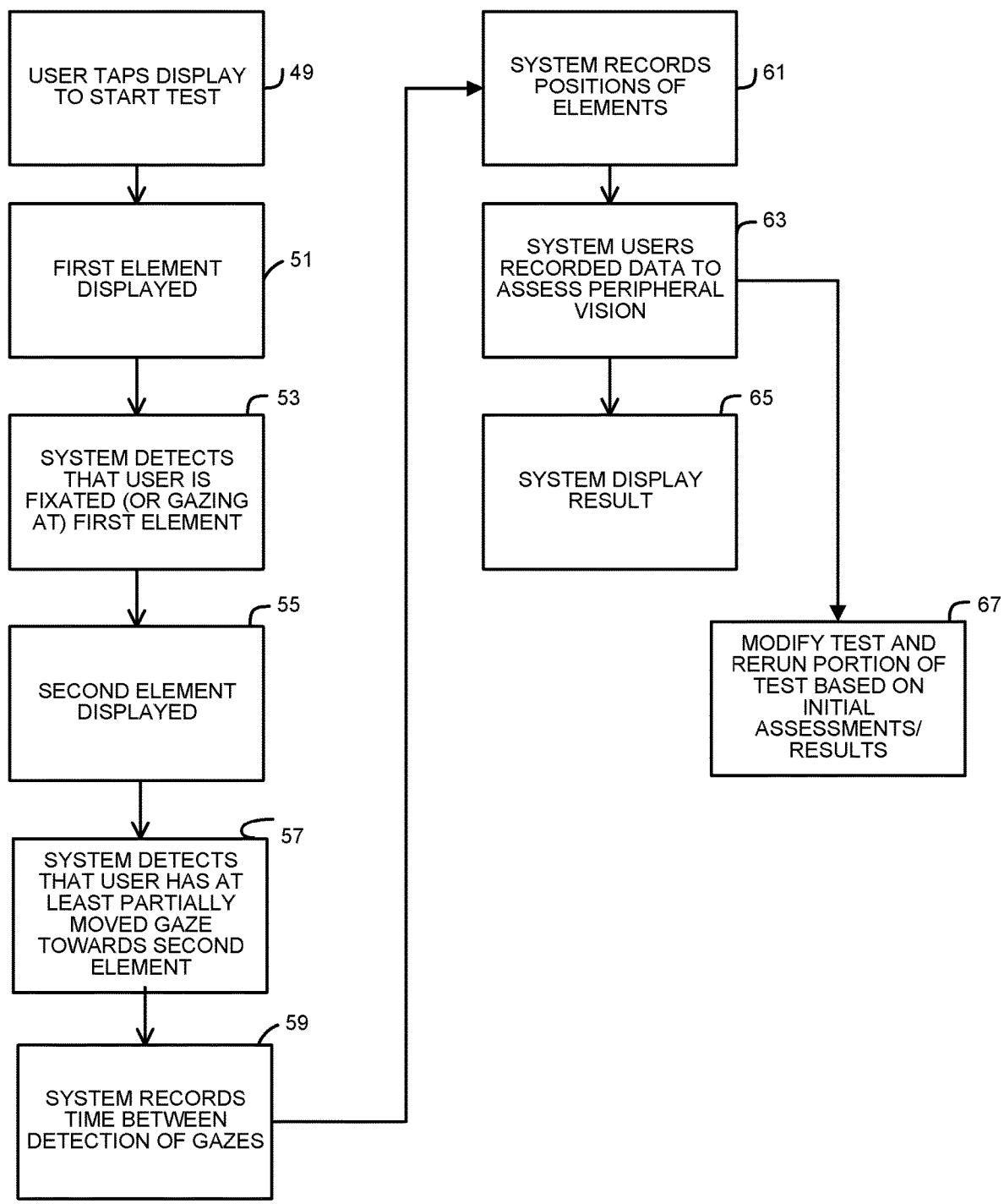
FIG. 4 is a flowchart illustrating a method in which the system of FIG. 2 may be employed.

FIG. 4 depicts a flow chart 30 which may be implemented by the system of FIG. 2. As before, a user may tap the display to start the test (step 49). But in this case a first element is displayed (step 51). Unlike the method of FIG. 3, the first element may be caused to disappear upon display or rendering of a second element. However, prior to this, the system detects that the user is fixated or is otherwise gazing at the first element (step 53). Subsequently, the first element is removed and a second element is displayed (step 55). As before, the system may detect that the user has at least partially move their gaze towards the second element (step 57). The system may record the time between the detection of gazes (step 59), e.g., the time at which gaze was detected at the first element and the time in which the gaze was detected at the second element. The system records the direction and distance of the saccade towards the second element. These steps may be repeated for third, fourth, fifth, and so on, elements. The system records the positions of the elements (step 61), as well as whether the user was able to detect viewing of the elements in their peripheral vision. The system records the direction and distance of the saccade towards the subsequent elements. The system may then use for the recorded data to assess the peripheral vision of the user (step 63). The system may display the result (step 65). As before, depending on the results of prior tests, a preprogrammed test may be modified and rerun based on an initial assessment and results (step 67).

Generally, in each of these embodiments, single flash elements are displayed sequentially, although the single flash elements may be separated by a span of time in alternative implementations. The single flash elements may appear for differing amounts of time, and in some cases more than one flash element may be displayed at one time.

In one implementation, details of the ways in which eye movements can be analyzed and tracked include those disclosed in US Patent Application entitled "SYSTEM AND METHOD FOR ANALYSIS OF EYE MOVEMENTS USING TWO-DIMENSIONAL IMAGES", as well as patent applications incorporated by reference therein, all of which are incorporated by reference herein. Other implementations may also be understood. In general, eye trackers may be employed which measure eye position or which measure the point of gaze. In an exemplary implementation, video-based eye trackers may be employed, in which a camera focuses on one or both eyes and records their movement. Such may also include infrared or near-infrared eye tracking techniques.

The system and method may be fully implemented in any number of computing devices. Typically, instructions are laid out on computer readable media, generally non-transitory, and these instructions are sufficient to allow a processor in the computing device to implement the method of the invention. The computer readable medium may be a hard drive or solid state storage having instructions that, when run, are loaded into random access memory. Inputs to the application, e.g., from the plurality of users or from any one user, may be by any number of appropriate computer input devices. For example, users may employ a keyboard, mouse, touchscreen, joystick, trackpad, other pointing device, or any other such computer input device to input data relevant to the calculations. Data may also be input by way of an inserted memory chip, hard drive, flash drives, flash memory, optical media, magnetic media, or any other type of file-storing medium. The outputs may be delivered to a user by way of a video graphics card or integrated graphics chipset coupled to a display that may be seen by a user. Alternatively, a printer may be employed to output hard copies of the results. Given this teaching, any number of other tangible outputs will also be understood to be contemplated by the invention. For example, outputs may be stored on a memory chip, hard drive, flash drives, flash memory, optical media, magnetic media, or any other type of output. It should also be noted that the invention may be implemented on any number of different types of computing devices, e.g., personal computers, laptop computers, notebook computers, net book computers, handheld computers, personal digital assistants, mobile phones, smart phones, tablet computers, and also on devices specifically designed for these purpose. In one implementation, a user of a smartphone or WiFi-connected device downloads a copy of the application to their device from a server using a wireless Internet connection. An appropriate authentication procedure and secure transaction process may provide for payment to be made to the seller. The application may download over the mobile connection, or over the WiFi or other wireless network connection. The application may then be run by the user. Such a networked system may provide a suitable computing environment for an implementation in which a plurality of users provide separate inputs to the system and method. In the below system where visual field testing is contemplated, the plural inputs may allow plural users to input relevant data at the same time.

The invention claimed is:

1. A method of testing the visual field of the user, comprising:
   (i) detecting a user input indicating that a visual field test should begin;
   (ii) displaying a first element on a display screen;
   (iii) detecting if a user's eye or eyes are looking at the first element, and determining a first time duration between the display of the first element and the detecting;
   (iv) repeating the displaying and detecting and determining steps for a plurality of subsequent sequential elements;
   (v) detecting one or more user saccade movements, the detected user saccade movements associated with angles, distances and timing; and
   (vi) determining an indication of a visual field of the user based on:
   (1) the determined time durations and the locations of the sequential elements and the distances therebetween; and
   (2) the angles and distances of user saccades.

2. The method of claim 1, further comprising if the user's eye or eyes are detected to be not looking at the displayed element, displaying an instruction to the user to look at the displayed element.

3. The method of claim 1, wherein the detecting if the user's eye or eyes are looking at the element includes detecting if the user's eye or eyes are fixated on the element.

4. The method of claim 1, wherein the detecting if the user's eye or eyes are looking at the element includes detecting if the user's eye or eyes moved in a direction towards the element.

5. The method of claim 4, wherein the detecting if the user's eye or eyes moved in a direction towards the element includes detecting if the user's eye or eyes moved in a direction from a previous element to the subsequent element.

6. The method of claim 1, further comprising determining a type of eye movement detected as part or all of the movement.

7. The method of claim 6, further comprising excluding certain types of eye movements from the detecting if a user's eye or eyes are looking at the element step.

8. A computer readable medium, comprising instructions for causing a computing environment to perform the method of claim 1.

9. The medium of claim 8, wherein the instructions are downloadable from an online resource.

10. The method of claim 1 further comprising performing steps (i)-(vi) for an initial assessment and repeating steps (i)-(vi) for a refined assessment based at least in part on the initial assessment.

11. The method of claim 10 wherein the initial assessment employs a predefined set of elements that are used to assess multiple users.

12. The method of claim 1 wherein detecting the one or more saccades includes detecting a plurality of saccades needed to complete fixation on a subsequent one of the sequential elements.

13. The method of claim 1 further comprising removing the first element from the display screen before displaying a subsequent one of the subsequent sequential elements.

14. The method of claim 1 wherein at least one display characteristic of the first element and/or a subsequent sequential element varies over time, the display characteristic being selected from the group consisting of color, contrast and size.

15. The method of claim 1 wherein at least one display characteristic of the first element and a subsequent sequential element are different from one another, the display characteristic being selected from the group consisting of color, brightness, contrast and size.

16. The method of claim 1 further comprising determining a measure associated with glaucoma, or an eye or vision or other sort of defect or malady involving the peripheral vision, based on the indication of the visual field.

17. The method of claim 14 wherein the at least one display characteristic of the first element and/or a subsequent sequential element that varies over time also includes brightness.

\* \* \* \* \*